United States Patent [19]

Lindquist, Sr.

[11] Plant 4,283

[45] Jul. 25, 1978

[54] ROSE PLANT

[75] Inventor: Robert V. Lindquist, Sr., Hemet, Calif.

[73] Assignee: The Conard-Pyle Company, West Grove, Pa.

[21] Appl. No.: 850,813

[22] Filed: Nov. 11, 1977

[51] Int. Cl.[2] ..... A01H 5/00

[52] U.S. Cl. ..... Plt./11

[58] Field of Search ..... Plt./11

*Primary Examiner*—Robert E. Bagwill
*Assistant Examiner*—James R. Feyrer
*Attorney, Agent, or Firm*—Burns, Doane, Swecker & Mathis

[57] ABSTRACT

A rose plant of the Hybrid Tea class originated by crossing Kordes Perfecta (U.S. Plant Pat. No. 1,604) with Belle Blonde.

1 Drawing Figure

SUMMARY OF THE INVENTION

My invention relates to a new and distinct variety of rose plant of the Hybrid Tea class originated by me as the result of a breeding program using Kordes Perfecta (U.S. Plant Pat. No. 1,604) as the seed parent and Belle Blonde as the pollen parent. This new variety initially has been designated 75 R 13. The variety name for this new variety is "Fireside".

As a result of this crossing, I have produced a new and useful rose variety which is distinguished from its parents, and all rose varieties of which I am aware, as evidenced by the following unique combination of characteristics:

1. A Hybrid Tea rose plant bearing blooms which display a very wide spectrum of color ranging from bright yellow at the center through near white to deep rose at the petal margins.

2. Highly glossy foliage.

Asexual reproduction of my new variety by budding at Hemet, Calif., shows that all characteristics of the new variety are established and transmitted through succeeding propagations.

BRIEF DESCRIPTION OF THE DRAWING

The accompanying drawing shows typical specimens of the vegetative growth and flowers of my new variety in different stages of development as depicted in color as nearly true as is reasonably possible to make the same in a color illustration of this character.

DETAILED DESCRIPTION OF THE VARIETY

The following is a detailed description of my new variety while grown in a greenhouse at Hemet, Calif., in May 1977. Color terminology is in accordance with the Colour Chart of the Royal Horticultural Society, London, England.

Class: Hybrid Tea.

Propagation: It holds its distinguishing characteristics through succeeding propagations by budding.

FLOWER

Blooming habit: recurrent, continuous.

Bud:

*Size.*—large.

*Form.*—ovoid.

*Color.*—When sepals first divide — near red — Group 46A. When petals begin to unfurl — near red — Group 44A with shadings of near yellow-orange — Group 22A and 22B. When half-blown: Inside of petals — from base of petal outward near yellow-orange Group 22B shading out to shades of near red — Group 52C and 54B to edge of inner petal. Reverse side of petals: Base of petal near yellow-orange Group 14B shading to near yellow — orange Group 22C and 22D. Slight rim of near red — Group 52A on the extreme outer edge of petal.

*Sepals.*—Approximately same length as bud. Some with and some without appendages. Color — near yellow-green Group 146B.

*Peduncle.*—Length — long approximately 5". Aspect — few prickles. Strength — erect medium thick. Color — near yellow-green group 146B.

Bloom:

*Size.*—Large from 5½ inches to 6 inches.

*Borne.*—Singly and several together.

*Form.*—High centered at first, petals remaining at first loosely rolled outward. Becoming flat at maturity.

*Petalage.*—Double 20 to 35 petals, becomes more single in hot weather.

*Color.*—Inner petals — at center of flower base of petals near yellow-orange Group 15C shading to near yellow-orange Group 22C outer edge of petals becoming shades of near red Group 52C and 54B. Outer petals — near yellow-orange Group 22A and 22B edged with shadings of near red-purple group 66C and 66D. Base of petals — near yellow-orange Group 17B. Reverse of petals near yellow-orange Group 22C. Near red-purple Group 58D on outer edge of petals. General tonality — multicolor bloom displays very wide spectrum of color going from yellow (center) through near white to deep rose on petal margins. Color changes — as bloom ages color starts fading to light shades of near yellow Group 10C and 10D with edges fading to near red-purple Group 66D. General tonality — light yellow center to magenta shadings on outer edge of petals.

*Petals.*—Texture — average thickness, lacks substance, does not hold up well in hot weather. Appearance — inside - velvety; outside - satiny. Form — round. Arrangement — regularly arranged shingle-like. Petaloids in center — few large. Persistence — drop off cleanly. Fragrance — mild — tea. Lasting quality — on plant - average. As cut flower — average.

REPRODUCTIVE ORGANS

Stamens: Many arranged regularly about pistils.
Filaments: Most with anthers, much longer than the stigmas — color — near yellow-orange Group 16A.
Anthers: Medium size. Color — near yellow-orange Group 26A.
Pollen: Near orange Group 26A.
Styles: Uneven lengths — thin.
Stigmas: Color — near yellow-orange Group 22 A.
Hips: Shape — globular. Size — large. Color — near greyed-orange Group 167C. Seeds do not protrude. Seeds per hip 18 to 24.

PLANT

Form: Bushy.
Growth: Vigorous.
Height attained: 6 ft.
Foliage: Compound of 5 to 7 leaflets.
*Size.*—Large.
*Quantity.*—Normal.
*Color.*—New foliage — upper side near greyed-purple Group 187B. Underside — near greyed purple Group 183B. Old foliage — upper side near yellow-green group 147A. Underside - near yellow-green Group 147B.
*Shape.*—Oblong-pointed apex.
*Texture.*—Upper side — thick glossy. Underside — thick dull.
*Edge.*—Serrated.

*Serration.*—Irregular.
*Leaf Stem.*—Color near yellow-green Group 146A. Underside near yellow-green Group 146C. Small hooked thorns hooking toward plant stem, spaced at intervals of approximately ½ inch.
*Stipules.*—Medium length, narrow slightly bearded.
*Resistance to disease.*—Blackspot — average. Mildew — average. Rust — average.
Wood:
*New wood.*—Color near yellow-green Group 146A. Bark — moderately smooth.
*Old wood.*—Color near yellow-green Group 148A. Bark — moderately rough.
*Thorns.*—Quantity on main stalks from base — ordinary. On laterals from stalk — average.
*Form.*—Narrow.
*Length.*—Medium.
*Color (when young).*—Near greyed-orange Group 173A.
*Position.*—Irregular.
*Prickles.*—Quantity on main stalks — few. On laterals — few.
*Winter hardiness.*—Average.

I claim:

1. A new and distinct variety of rose plant of the Hybrid Tea class substantially as herein shown and described, characterized particularly as to novelty by (1) blooms which display a very wide spectrum of color ranging from bright yellow at the center through near white to deep rose at the petal margins, and (2) highly glossy foliage.

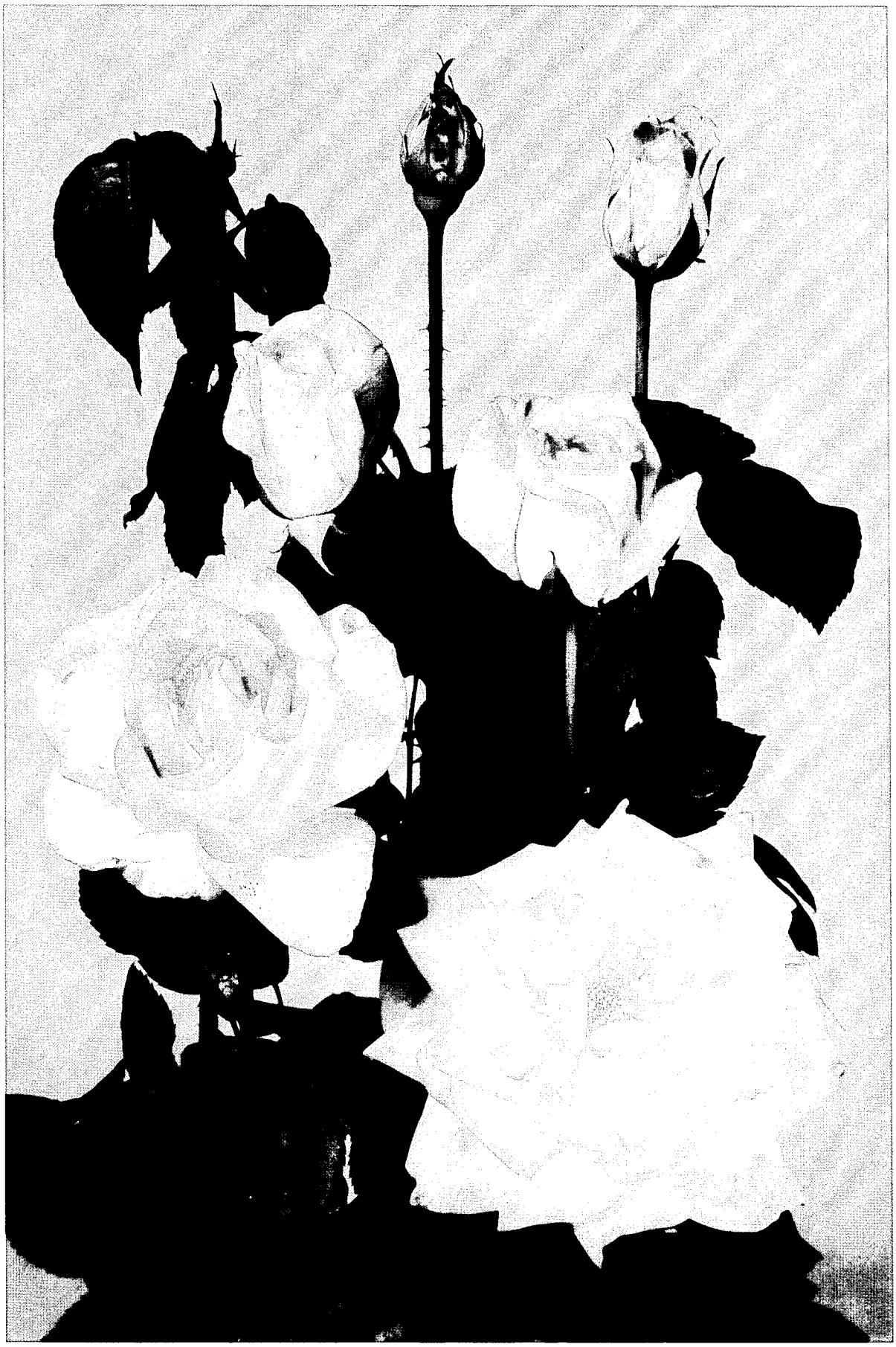

* * * * *